United States Patent [19]
Schutt

[11] Patent Number: 5,177,004
[45] Date of Patent: Jan. 5, 1993

[54] ENZYMATIC DEACYLATION OF ACYL-AMINOSORBOSES

[75] Inventor: Hermann Schutt, Wuppertal, Fed. Rep. of Germany

[73] Assignee: Bayer Aktiengesellschaft, Leverkusen, Fed. Rep. of Germany

[21] Appl. No.: 757,867

[22] Filed: Sep. 11, 1991

[30] Foreign Application Priority Data

Sep. 22, 1990 [DE] Fed. Rep. of Germany ....... 4030040

[51] Int. Cl.⁵ ..................... C12P 19/26; C12P 19/28; C12N 9/80; C07H 5/06
[52] U.S. Cl. ........................ 435/84; 435/85; 435/228; 435/229; 435/230
[58] Field of Search ............... 435/84, 85, 230, 228, 435/229

[56] References Cited

U.S. PATENT DOCUMENTS

| | | |
|---|---|---|
| 3,880,713 | 4/1975 | Fleming et al. ............... 435/230 |
| 3,930,949 | 1/1976 | Kutzbach et al. ............. 435/230 |
| 3,962,036 | 6/1976 | Liersch et al. ............... 435/230 |
| 4,264,734 | 4/1981 | Kahan et al. ................ 435/228 |
| 4,282,322 | 8/1981 | Kahan et al. ................ 435/228 |
| 4,405,714 | 9/1983 | Kinast et al. ................ 435/84 |
| 4,806,650 | 2/1989 | Schroder et al. ............. 435/84 |
| 4,981,789 | 1/1991 | Lein ......................... 435/228 |

FOREIGN PATENT DOCUMENTS 0049858 4/1982 European Pat. Off. .
0240868 10/1987 European Pat. Off. .

Primary Examiner—Herbert J. Lilling
Attorney, Agent, or Firm—Sprung Horn Kramer & Woods

[57] ABSTRACT

The present invention relates to an improved process for the preparation of 1-desoxynojirimycin. 1-Desoxynojirimycin can be reacted by alkylation on the nitrogen atom to give various saccharase inhibitors which are used therapeutically in the treatment of diabetes mellitus.

1 Claim, 1 Drawing Sheet

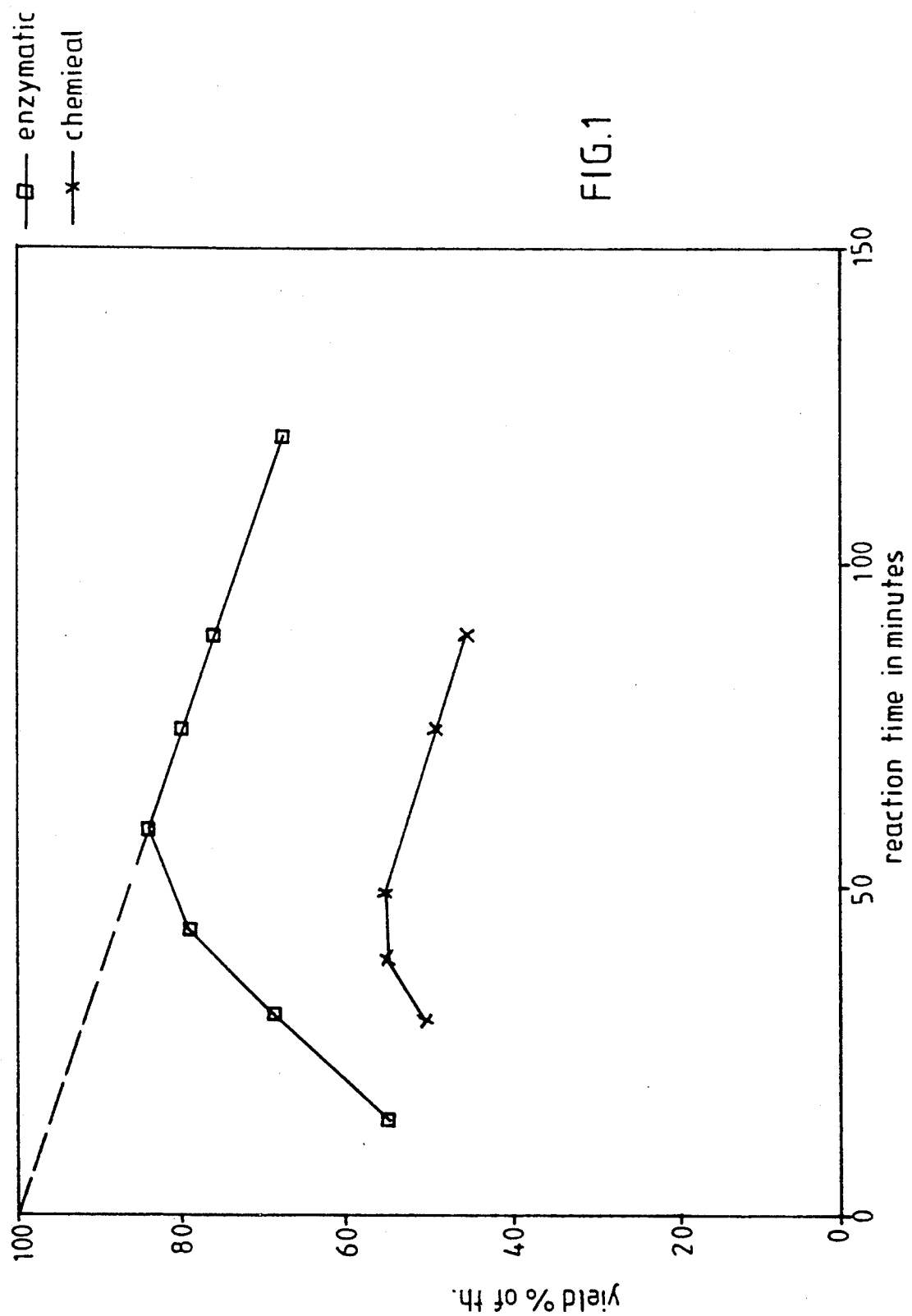

ENZYMATIC DEACYLATION OF ACYL-AMINOSORBOSES

The present invention relates to an improved process for the preparation of 1-desoxynojirimycin. 1-Desoxynojirimycin can be reacted by alkylation on the nitrogen atom to give various saccharase inhibitors which are used therapeutically in the treatment of diabetes mellitus (W. Puls, U. Keup, H.P. Krause, G. Thomas, and F. Hoffmeister, Naturwissenschaften, 64 (1977) 536 et seq.).

1-Desoxynojirimycin is prepared by a combined chemical-microbiological process (EP 49,858).

An important intermediate in the preparation of 1-desoxynojirimycin is aminosorbose, which, however, is unstable. To remove the N-acetyl and N-formyl protecting group, either extremely acidic or extremely alkaline conditions have to be selected. Above pH 2 and below pH 13, virtually no removal of the acyl group takes place. Under the abovementioned pH conditions, however, considerable desoxyno3irimycin losses are observed. These result on the one hand from cyclisation reactions of the aminosorbose itself to give, for example, hydroxylated pyridines, on the other hand, coloured secondary components which have not been specified in more detail are formed. Thus, on acidic removal of the acyl group only a yield of about 27 % of desoxynojirimycin was observed and on alkaline removal a yield of about 60 % of desoxynojirimycin was observed.

SUMMARY OF THE INVENTION

Surprisingly, it has now been found that in the range from 8 to 9.5, the removal of an N-phenacetyl protecting group by means of the known enzyme penicillin acylase (penicillin amidohydrolase (EC 3.5.1.11)) isolated from Escherichia coli can be achieved with substantially better yield and purity of 1-desoxynojirimycin than with chemical methods.

BRIEF DESCRIPTION OF THE DRAWINGS

FIG. 1 is a graph comparing the yield of 1-desoxynojirinycin over time when prepared by chemical methods and enzymatic methods.

DETAILED DESCRIPTION OF THE INVENTION

The reaction mentioned is described by the following reaction equations:

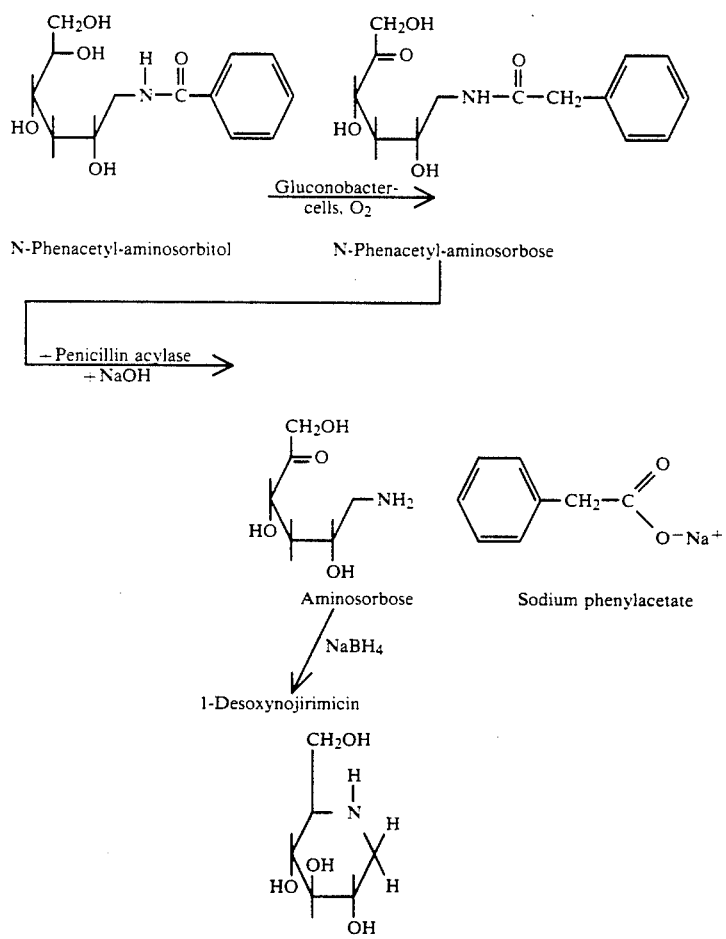

At pH 13, in contrast to pH 8-9, a very rapid decomposition of aminosorbose is observed, which leads to the loss of 40-50 % of 1-desoxynojirimycin.

In the enzymatic removal of the N-phenacetyl protecting group using penicillin acylase, however, this rapid decomposition is lacking, so that the yield of 1-desoxynojirimycin can be increased. The yield can be still further increased by an increase in the enzyme concentration and thus a reduction of the cleavage time (FIG. 1).

Penicillin acylase has hitherto only been described for the removal of the N-phenacetyl group on penicillin and cephalosporin parent substances, amino acids and peptides (J.G. Shewale, B.S. Deshphande, V.K. Sudhakaran and S.S. Ambedkar, Process Biochemistry, June 1990, 97–103).

The removal of the phenacetyl group from amino sugars using penicillin acylase is new and also utilisable for other unstable N-acyl-aminopentoses and aminohexoses.

In the process described, purified free and carrier-bound penicillin acylase, for example, can be employed.

EXAMPLE 1

Use of soluble penicillin acylase 3 kg of N-phenacetyl-aminosorbitol are dissolved in 150 litres of water and the pH of the solution is adjusted to about 4.5 and kept at this pH. The solution is warmed to 37° C. and about 6 kg of centrifuged bacterial cells (Gluconobacter suboxydans) are added and the suspension is aerated intensively with air whilst stirring for 4 hours.

In this period, the N-phenacetyl-aminosorbitol is quantitatively oxidised to N-phenacetyl-aminosorbose microbiologically. The Gluconobacter cells are completely removed from the suspension by centrifugation, the clear supernatant is adjusted to pH 9 using sodium hydroxide solution and 2.7 million units of penicillin acylase are added (isolation of the enzyme and definition of the unit are described in the literature reference: C. Kutzbach and E. Rauenbusch, Hoppe-Seyler's Z. Physiol.-Chem., 354 (1974) 45–53). The removal of the phenylacetic acid is monitored by means of high pressure liquid chromatography via the determination of the liberated phenylacetic acid and/or the decrease in the N-phenacetylaminosorbose. After a reaction time of about 45–60 minutes, the removal of protecting groups is complete and 270 g of sodium borohydride are added. Reduction and cyclisation to give 1-desoxynojirimycin last 60 minutes. The excess of sodium borohydride is then destroyed by addition of acetone or HCl.

Further working-up to give pure 1-desoxynojirimycin is carried out by chromatography via ion exchangers and subsequent crystallisation as described in EP 49,859 and in the literature reference: Y. Eze, S. Maruo, K. Miyazaki and M. Kawamata, Agric. Biol. Chem., 49 (1985) 1119–1125.

After crystallisation, about 1.3 kg of 1-desoxynojirimycin (about 80 % molar yield) having a purity by HPLC >95 % are obtained.

EXAMPLE 2

Use of carrier-bound penicillin acylase Carrying-out takes place as described in Example 1. To remove the N-phenacetyl group, 5.0 million units of penicillin acylase resin prepared according to DOS (German Offenlegungsschrift) 2,215,687 are added. Before the isolation of 1-desoxynojirimycin, the enzyme resin is filtered off and washed.

The yield of 1-desoxynojirimycin is 1.4 kg (about 83 % molar yield) having a purity of HPLC>95%.

| High pressure liquid chromatography | | |
|---|---|---|
| Column: | | |
| LiChrospher RP 18.5 μm | | |
| (Merck, Darmstadt): | | |
| 250 mm × 4 mm | | |
| Eluent: | | |
| A: 0.05 M phosphate, pH 6.5 | | |
| B:90% acetonitrile: 10% water | | |
| Gradient: | | |
| Time in min. | % A | % B |
| 0 | 100 | 0 |
| 2 | 100 | 0 |
| 10 | 0 | 100 |
| 11.5 | 0 | 100 |
| 11.6 | 100 | 0 |
| 16.5 | 100 | 0 |
| Flow rate: 1.5 ml/min. | | |
| Temperature: 25° C. | | |
| Wavelength: 210 nm | | |
| Injection volume: 20 μL | | |
| Retention times in minutes: | | |
| N-phenacetyl-aminosorbitol: | | 7.1 |
| N-phenacetyl-aminosorbose: | | 8.7 |
| Phenylacetic acid: | | 4.7 |
| Desoxynojirimycin: | | 0.9 |

I claim:

1. A process for preparing aminosorbose comprising enzymatically deacylating N-phenylacetyl-aminosorbose with pencillin acylase at a pH of from about 8 to 9.5.

* * * * *